(12) United States Patent
Chin et al.

(10) Patent No.: US 7,641,631 B2
(45) Date of Patent: Jan. 5, 2010

(54) DILATATION BALLOON HAVING A VALVED OPENING AND RELATED CATHETERS AND METHODS

(75) Inventors: Yem Chin, Burlington, MA (US); Paul Scopton, Winchester, MA (US); Liem Vu, Needham, MA (US)

(73) Assignee: SCIMED Life Systems, Inc., Maple Grove, MN (US)

( * ) Notice: Subject to any disclaimer, the term of this patent is extended or adjusted under 35 U.S.C. 154(b) by 1119 days.

(21) Appl. No.: 10/778,108

(22) Filed: Feb. 17, 2004

(65) Prior Publication Data

US 2005/0182359 A1   Aug. 18, 2005

(51) Int. Cl.
*A61M 29/00*   (2006.01)
(52) U.S. Cl. .................................. 604/96.01
(58) Field of Classification Search ............... 604/96.01, 604/99.02, 99.03, 101.01–102.03, 915, 916, 604/917, 919; 606/191–194
See application file for complete search history.

(56) References Cited

U.S. PATENT DOCUMENTS

| | | | |
|---|---|---|---|
| 4,638,805 A | 1/1987 | Powell | |
| 4,715,378 A | 12/1987 | Pope, Jr. et al. | |
| 4,793,350 A | 12/1988 | Mar et al. | |
| 4,821,722 A | 4/1989 | Miller et al. | |
| 5,324,263 A | 6/1994 | Kraus et al. | |
| 5,387,225 A | 2/1995 | Euteneuer et al. | |
| 5,397,305 A * | 3/1995 | Kawula et al. | ........... 604/96.01 |
| 5,728,065 A * | 3/1998 | Follmer et al. | ........... 604/96.01 |
| 5,792,118 A | 8/1998 | Kurth et al. | |
| 5,807,328 A | 9/1998 | Briscoe | |
| 2002/0099408 A1 | 7/2002 | Marks et al. | |
| 2002/0193742 A1 | 12/2002 | Davey | |

FOREIGN PATENT DOCUMENTS

WO    WO 02/058781 A2    8/2002

* cited by examiner

*Primary Examiner*—Manuel A Mendez
(74) *Attorney, Agent, or Firm*—Finnegan, Henderson, Farabow, Garrett & Dunner, L.L.P.

(57) ABSTRACT

Dilation catheters including a mechanism used in, for example, removing gas or air from the catheters are disclosed. A dilation catheter may include an elongated tubular member having a distal end and a proximal end, a proximal handle proximate the proximal end of the tubular member, and an inflatable balloon proximate the distal end of the tubular member with inflatable balloon being in fluid communication with a fluid port to supply inflation liquid to the inflatable balloon. The inflatable balloon may include an opening for permitting gas to exit the inflatable balloon. In the proximate location of the opening, an expandable material or a barrier material that permits gas to exit through the opening, while retaining inflation liquid in the inflatable balloon.

39 Claims, 5 Drawing Sheets

DILATATION BALLOON HAVING A VALVED OPENING AND RELATED CATHETERS AND METHODS

FIELD OF THE INVENTION

This invention relates to dilation catheters and related methods thereof. In a particular embodiment, the invention relates to methods and apparatuses for removing air from a balloon dilation catheter prior to insertion of the catheter into a patient's body.

DESCRIPTION OF THE RELATED ART

Balloon dilation catheters have a number of different medical applications, such as, for example, deployment of medical stents and dilation of restricted body lumens. Currently, a wide variety of balloon dilation catheters are being used, the functions and operational characteristics of which are primarily dependent upon the type of medical procedure being performed.

For example, during an intravascular medical procedure, such as, for example, an angioplasty procedure, a balloon dilation catheter may be used to eliminate or reduce a narrowing in an artery by placing an inflatable balloon in the location of narrowing and inflating the balloon to enlarge the narrowing of the artery. Prior to the catheter insertion into the body, however, the catheter may require a prepping procedure to remove all of the air trapped inside the catheter. This is because the air (e.g., in the form of air bubbles) trapped in the catheter may raise a number of safety and operational issues. In particular, if the trapped air leaks into a blood vessel by, for example, balloon rupture or sealing failure, the leaked air, being compressible, may expand rapidly, causing obstruction of blood flow (known as air emboli) and causing a serious harm to the patient. In addition, the air trapped inside the balloon and a fluid lumen used for transporting the inflation liquid may disturb the steady flow of the inflation liquid, thereby hindering efficient balloon inflation and deflation. If the balloon inflation and deflation are prolonged substantially, the condition may result in an inadvertent, prolonged blockage of the artery, possibly causing harm to the patient.

Thus, a prepping procedure to remove air from the catheter is required by physicians or nurses prior to insertion of the catheter into a patient's body. Prepping a balloon dilatation catheter may typically involve removing the air from the catheter by pulling a vacuum on the proximal end of the catheter or injecting a liquid into the balloon and rotating the catheter vertically so as to allow air in the catheter to exit through an opening at a proximal end portion. These methods of removing air, however, generally involve a number of cumbersome processes and often are ineffective in completely removing the air from the catheter.

As a prepping procedure for removing air from a balloon dilatation catheter, a catheter having a small opening at the distal tip of the inflatable balloon has been proposed. The opening allows the air trapped inside the balloon to exit through the opening as the catheter is prepped outside of the patient prior to insertion. However, the opening remains open even during the inflation procedure inside the patient, permitting a small amount of the inflation liquid to "weep" through the opening. This weeping requires a continuous injection of inflation liquid in order to compensate for the leaked inflation liquid and maintain the dilation pressure.

SUMMARY OF THE INVENTION

Therefore, an embodiment of the invention relates to a balloon dilation catheter that addresses the above-mentioned problems by providing a mechanism which may selectively allow removal of the air trapped inside the catheter without losing any inflation liquid. While the present invention will be described in connection with a balloon dilation catheter, the invention may be applied to any other types of catheters or devices that may require selective removal of air or gas, such as, for example, fluid injection catheters or drug dispensing devices. The invention may also be applied to numerous other catheters and devices utilizing the balloon expansion mechanism, such as, for example, stent placement/deployment catheters, dilatation-ureteral balloon catheters, nephrostomy balloon catheters, or latex balloon occlusion catheters, or other suitable medical devices that require a sealing process, such as, for example, a drug dispensing device for sealing a drug delivery path after dispensing a drug.

To attain the advantages and in accordance with the purpose of the invention, as embodied and broadly described herein, one aspect of the invention may provide a balloon assembly for a medical device, comprising an inflatable balloon, a fluid port in fluid communication with the inflatable balloon to supply inflation liquid to the inflatable balloon, an opening for permitting gas to exit the inflatable balloon, and an expandable material having a first configuration configured to permit gas to exit through the opening and a second configuration configured to retain inflation liquid in the inflatable balloon. The opening may be located at a distal-most end of the inflatable balloon. The opening may be formed by a hollow tube extending from the inflatable balloon.

In another aspect of the invention, the expandable material may include a liquid-activatable material configured to close the opening upon contact with inflation liquid. The expandable material may be configured to close the opening after substantially all of the gas is removed from the inflatable balloon through the opening. The expandable material may have a material characteristic of expanding in volume from the first configuration to the second configuration upon contact with inflation liquid. The expandable material may also be configured to expand from the first configuration to the second configuration in response to contact with a bonding agent or catalyst of an inflation liquid. Prior to the contact with inflation liquid, the expandable material may remain in the first configuration without interfering with the passage of gas through the opening. The expandable material may be spaced from the opening in the first configuration, so that, prior to contact with inflation liquid, the material may not block the opening, but after contact with inflation liquid, the material may expand to the second configuration and substantially close the opening.

In still another aspect of the invention, the expandable material may include an occlusive material. The occlusive material may include a plurality of beads, which may be interconnected.

According to another aspect of the invention, the expandable material may be on an inside surface of the hollow tube. Prior to contact with inflation liquid, the material may remain in the first configuration and may not block the opening. After contact with inflation liquid, however, the material may expand to the second configuration and substantially close the opening. In an aspect, the expandable material may be coated on the inside surface of the hollow tube.

In still another aspect of the invention, the expandable material may include a hydrophilic material placed proximate the opening. The expandable material may be disposed in the form selected from the group consisting of particles, coating, porous matrix, fiber bundles, tubular bed, and any combination thereof.

In yet still another aspect of the invention, the expandable material may be selected from a group consisting of: super absorbent polymers; hydrogel polymers; water-swellable polymers; hydrocolloids; hydrocolloids having polymer compositions of substantially water-insoluble, slightly cross-linked, partially neutralized polymers prepared from unsaturated polymerizable acid group-containing monomers and cross-linking agents; polymer materials that have undergone a cross-linking process; polyacrylates; PEG; polysaccharides; starch or cellulose; generally carboxyl containing polymers; hydrolyzates of starch-acrylonitrile graft copolymers; partially neutralized products of starch-acrylic acid or polyvinyl alcohol graft copolymers; saponification products of vinyl acetate acrylic ester copolymers; derivatives of copolymers of isobutylene and maleic anhydride; hydrolyzates of acrylonitrile copolymers; cross-linked products of hydrolyzates of acrylonitrile copolymers; cross-linked carboxymethyl cellulose; polyaspartate hydrolyzates of acrylamide copolymers; cross-linked products of hydrolyzates of acrylamide copolymers; partially neutralized products of polyacrylic acids; cross-linked products of partially neutralized polyacrylic acids; natural non-ionic polymers; carraggeenan; xanthan gum; gelatin; agar; alginate; and any combination thereof.

Another aspect of the invention may provide a balloon assembly for a medical device, comprising an inflatable balloon, a fluid port in fluid communication with the inflatable balloon to supply inflation liquid to the inflatable balloon, an opening for permitting gas to exit the inflatable balloon, and a barrier material disposed on the opening and configured to allow gas to pass through the opening while preventing passage of inflation liquid therethrough. In another aspect of the invention, the barrier material may be selected from a group consisting of: papers, porous-type ceramics, fabrics, foams, filter materials, and any combination thereof.

Still another aspect of the invention may provide a dilation catheter comprising an elongated tubular member having a distal end and a proximal end, a proximal handle proximate the proximal end of the tubular member, an inflatable balloon proximate the distal end of the tubular member with inflatable balloon being in fluid communication with a fluid port to supply inflation liquid to the inflatable balloon, the inflatable balloon including an opening for permitting gas to exit the inflatable balloon, and an expandable material having a first configuration configured to permit gas to exit through the opening and a second configuration configured to retain inflation liquid in the inflatable balloon.

In another aspect, the proximal handle may include a connection to a source of inflation liquid. The tubular member may include a lumen in fluid communication between the source of inflation liquid and the fluid port. Alternatively or additionally, the tubular member may define the fluid port.

In still yet another aspect of invention, a dilation catheter comprising an elongated tubular member having a distal end and a proximal end, a proximal handle proximate the proximal end of the tubular member, an inflatable balloon proximate the distal end of the tubular member with inflatable balloon being in fluid communication with a fluid port to supply inflation liquid to the inflatable balloon, the inflatable balloon including an opening for permitting gas to exit the inflatable balloon, and a barrier material disposed on the opening and configured to allow gas to pass through the opening while preventing passage of inflation liquid therethrough, may be provided. The barrier material may be selected from a group consisting of: papers, porous-type ceramics, fabrics, foams, filter materials, and any combination thereof.

In accordance with another aspect of the invention, a method of removing gas from a medical device may be provided. The method may include injecting a liquid into the medical device so as to force the gas in the medical device to exit through an opening, and after the gas is removed from the medical device, substantially closing the opening. The medical device may include an inflatable balloon, and the opening may be formed by the inflatable balloon.

In still another aspect, the method may also include orienting the device so that the opening may be located at a substantially highest elevation of the inflatable balloon. Injecting the liquid may force the gas in the medical device to exit through the opening.

According to yet still another aspect of the invention, the step of substantially closing the opening may include contacting a liquid-activated valve with the liquid. The liquid-activated valve may be positioned proximate the opening and may be configured to substantially close the opening upon contact with the liquid. The liquid-activated valve may include a self-expandable material configured to expand upon contact with the liquid.

In another aspect of the invention, the method may include deflating the inflatable balloon by withdrawing the liquid and/or inflating the inflatable balloon by injecting the liquid.

Still another aspect of the invention may provide a method of removing gas from a dilation catheter. The method may include providing a dilation catheter comprising an elongated tubular member having a distal end and a proximal end, a proximal handle proximate the proximal end of the tubular member, and an inflatable balloon proximate the distal end of the tubular member with inflatable balloon being in fluid communication with a fluid port to supply inflation liquid to the inflatable balloon, the inflatable balloon including an opening for permitting gas to exit the inflatable balloon. The method may also include injecting inflation liquid into the balloon through the fluid port so as to force the gas in the dilation catheter to exit through the opening, and after the gas is removed from the dilation catheter, substantially closing the opening.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

In the drawings.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

Figure 1:
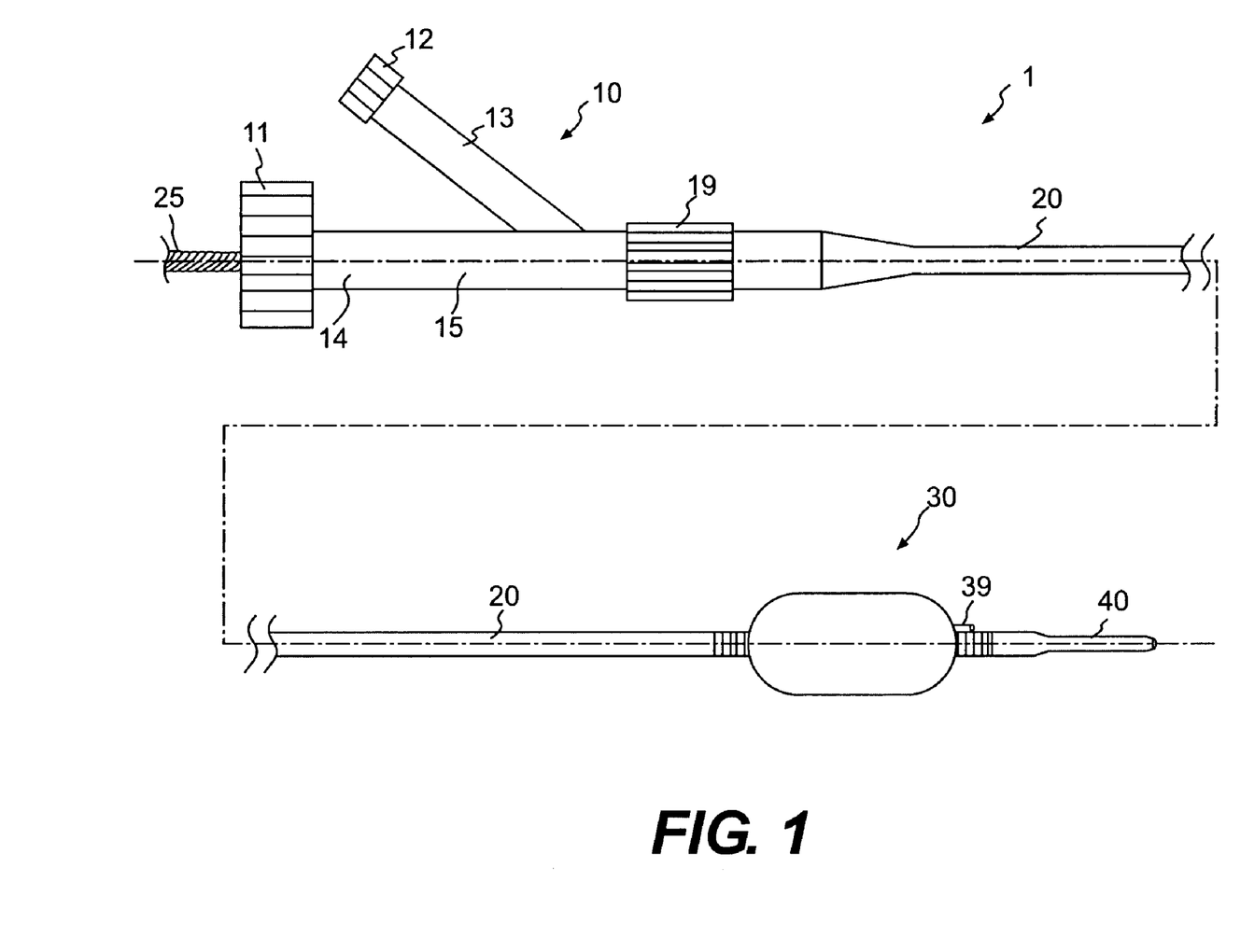
FIG. 1 is a schematic side view of a balloon dilation catheter, according to an embodiment of the invention.

According to an exemplary embodiment of the invention, FIG. 1 illustrates a balloon dilation catheter 1 having an air-ventilation opening 39 used to remove air from the catheter 1, for example, during a prepping procedure performed prior to insertion of the catheter 1 into a patient's body. While the invention will be described in connection with a particular balloon dilation catheter, the invention may be applied to, or used in connection with, any other types of balloon dilation catheters, numerous other catheters utilizing a balloon expansion mechanism, such as, for example, stent placement/deployment catheters, dilatation-ureteral balloon catheters, nephrostomy balloon catheters, or latex balloon catheters (e.g., occlusion balloons of Boston Scientific Corporation), or other suitable medical devices that require a sealing process, such as, for example, drug dispensing devices for sealing a drug delivery path after dispensing a drug, or that require removal of air or gas from the devices, such as, for example, fluid injection catheters or drug dispensing device.

As shown in FIG. 1, the balloon dilation catheter 1 may include an elongated flexible tubular member 20, a proximal handle assembly 10 coupled to a proximal end of the tubular member 20, and an inflatable balloon 30 attached to the distal end portion of the tubular member 20. The catheter 1 may be used with a flexible guide member 25, such as, for example, a wire, for guiding insertion of the catheter 1 through a body lumen. The distal tip portion 40 of the catheter 1 may be tapered so as to facilitate the insertion of the catheter 1 through the body lumen.

The handle assembly 10 may include a T- or Y-connector 15 having a main port 14 for receiving the guide member 25 and a side port 13 for connecting to a source of pressurized inflation liquid (not shown). The inflation liquid may include a saline solution, dye solution, water, or any other suitable liquid medium known in the art. In an embodiment, a syringe device (not shown) having a pressure gauge may be used to inject and retract the inflation liquid, while monitoring the balloon pressure. Any other device suitable for injecting inflation liquid may be used.

Each of the main port 14 and the side port 13 may include a suitable connector 11, 12, such as a luer-type connector or threaded connector. The connector 11, 12 may also include a sealing member (not shown) to prevent any leakage from the catheter 1. The handle assembly 10 may include a connecting member 19 that allows detachment of the connector 15 and/or replacement of the connector 15 with any other suitable connector, such as, for example, a connector having more than two ports.

The handle assembly 10 and the tubular member 20 may include a plurality of lumens for separately accommodating the guide member 25 and the inflation liquid. In an exemplary embodiment, the tubular member 20 may include a fluid lumen 31 (see FIG. 2) that is in fluid communication with the side port 13 of the handle assembly 10. The guide member 25 may extend from the main port of the handle assembly 10, pass through a lumen of the tubular member 20, preferably separate from the fluid lumen 31, and extend to the distal tip portion 40.

Figure 2:
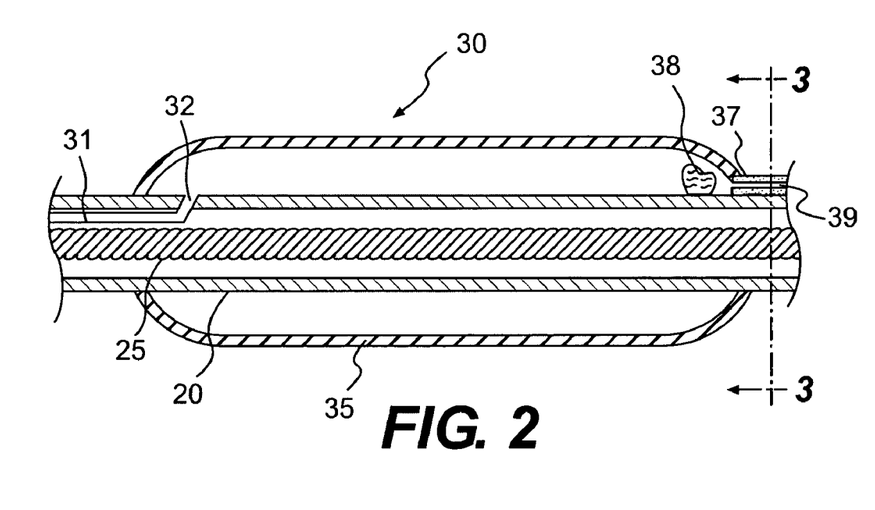
FIG. 2 is a cross-sectional view of the inflatable balloon of the balloon dilation catheter shown in FIG. 1, illustrating the balloon in a deflated state.
Figure 3:
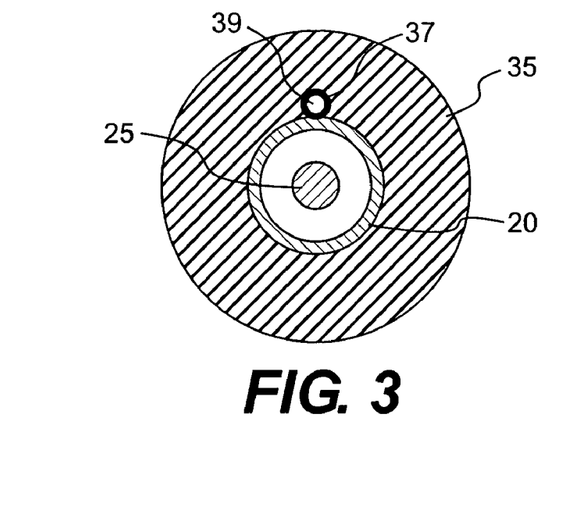
FIG. 3 is a frontal view taken from a plane (3-3) of FIG. 2, showing an air-ventilation opening.

As shown in FIGS. 2 and 3, the inflatable balloon 30 may be attached to or integrally formed with the tubular member 20. Alternatively, the inflatable balloon 30 may also be detachably coupled to the tubular member 20. The tubular member 20 may include a fluid port 32, through which the inflation liquid may be injected into the balloon 30. The balloon 30 may be formed of any suitable material having a sufficient tensile strength to sustain a desired pressure in the balloon 30, while maintaining a relatively thin wall thickness 35 in order to have a low deflated profile of the balloon 30. Possible materials for the balloon may include thermoplastic polymers, such as, for example, polyethylene terephthalate (PET), polyurethanes, polyethylenes and ionomers, copolyesters, rubbers, polyamides, or any other suitable materials known in the art.

At the distal end of the balloon 30, an opening 39 or slot may be formed for use in, for example, ventilating air out of the balloon 30. In an exemplary embodiment shown in FIGS. 2 and 3, the opening 39 may be formed with a tubular member 37 (e.g. a capillary tube) extending from the inside of the balloon 30 to the outside. While the figure shows only one opening 39, the balloon 30 may include a plurality of openings or slots. The opening 39 may be positioned at the distal-most end of the balloon 30 (i.e., at the highest elevation when the balloon is oriented vertically), so as to allow all of the air forced to the top of the balloon 30 to be completely removed through the opening 39 when the inflation liquid fills up the balloon 30. Alternatively, an opening 39 may be position at a location other than the distal-most end of the balloon 30.

Figure 4A:
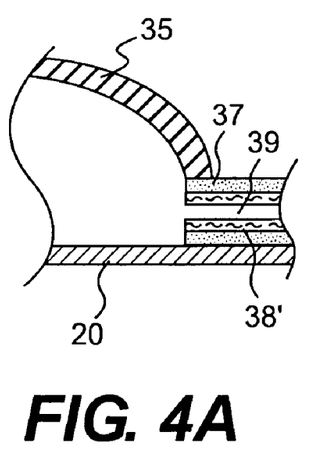
FIG. 4A is a partial exploded cross-sectional view of the distal end portion of the inflatable balloon, according to another embodiment of the invention, with an air-ventilation opening in an open state.
Figure 4B:
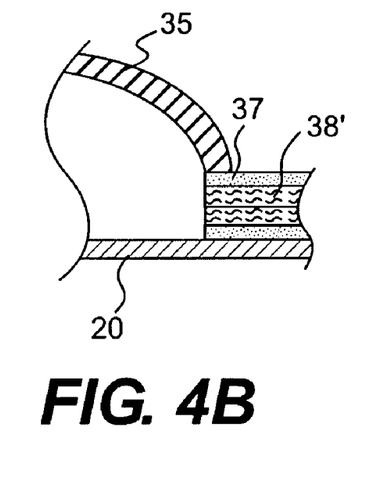
FIG. 4B is a partial exploded cross-sectional view of the distal end portion of the inflatable balloon shown in FIG. 4A with the air-ventilation opening in a closed state.

According to an embodiment of the invention, the inflatable balloon 30 may include a hydrophilic material 38 placed on, or in the vicinity of, the opening 39, as shown in FIGS. 2 and 4A-B, for example. The material 38 may function as a liquid-activated sealing valve for selectively permitting the air to exit the balloon 30, while retaining the inflation liquid in the balloon 30. The hydrophilic material 38 may be placed or deposited in the form of particles, coating, porous matrix, fiber bundles, tubular bed, or any other suitable means known in the art. Hydrophilic materials may have a unique material characteristic of absorbing moisture and self-expanding in volume after being exposed to an aqueous atmosphere. Owing to this moisture-sensitive expansion characteristic, the hydrophilic material 38 may be used to selectively permit removal of only the trapped air out of the balloon 30.

For example, as will be described later in further detail, the catheter 1 may be aligned vertically with the opening 39 positioned at the highest elevation. A suitable inflation liquid, injected through the side port 13, may pass through the fluid lumen 31 and into the balloon 30. The injection of the inflation liquid may force the air in the lumen 31 and the balloon 30 to be collected at the distal portion of the balloon 30. As the injection of the inflation liquid continues, the air trapped at the distal portion of the balloon 30 may then be forced out of the balloon 30 via the opening 39. When the inflation liquid level reaches the location where the hydrophilic material 38 may be placed, which occurs preferably after all or substantially all of the air in the balloon 30 has been removed, the inflation liquid may be brought into contact with the hydrophilic material 38, causing expansion of the material 38, preferably rapid or immediate expansion, and substantially sealing the opening 39. At this condition, the hydrophilic material 38 may expand, effectively occluding the opening 39 without requiring any additional bonding agent. Before the initial contact between the inflation liquid and the hydrophilic material 38, the hydrophilic material 38 may remain in its original shape and size without interfering with the passage of air through the opening 39.

Suitable materials having the liquid-activatable expansion capability include, but are not limited to the following: super absorbent polymers; hydrogel polymers; water-swellable polymers; hydrocolloids that are polymer compositions of substantially water-insoluble, slightly cross-linked, partially neutralized polymers prepared from unsaturated polymerizable acid group-containing monomers and cross-linking agents; or any other materials known in the art.

In particular, the polymer materials that have undergone a cross-linking process may have a relatively high gel volume and a relatively high gel strength upon contacting a liquid. The degree of cross-linking in hydrogel (or hydrophilic) and hydrogel-forming materials may be an important factor in establishing characteristics of liquid absorbing hydrogels, i.e., absorbent capacity and gel strength. Absorbent capacity of "gel volume" is a measure of the amount of water or body liquid that a given amount of hydrogel-forming material will absorb. Gel strength relates to the tendency of the hydrogel formed from such material to deform or flow under an applied stress. Since the materials have different expansion rates, the time it takes to expand and completely occlude the opening 39 may be controlled by properly selecting a suitable material.

Suitable polymers may include: polyacrylates; PEG; polysaccharides; starch or cellulose; generally carboxyl containing polymers; and any other suitable polymers known in the art. Examples of carboxyl-containing water absorbent polymers may include, but not be limited to: hydrolyzates of starch-acrylonitrile graft copolymers; partially neutralized products of starch-acrylic acid or polyvinyl alcohol graft copolymers; saponification products of vinyl acetate acrylic ester copolymers; derivatives of copolymers of isobutylene and maleic anhydride; hydrolyzates of acrylonitrile copolymers; cross-linked products of hydrolyzates of acrylonitrile copolymers; cross-linked carboxymethyl cellulose; polyaspartate hydrolyzates of acrylamide copolymers; cross-linked products of hydrolyzates of acrylamide copolymers; partially neutralized products of polyacrylic acids; and cross-linked products of partially neutralized polyacrylic acids. Alternatively or additionally, natural non-ionic polymers, such as, for example, carraggeenan, xanthan gum, gelatin, agar, and alginate, may also be used.

In an exemplary embodiment, the hydrophilic material 38 may be mixed with a suitable occlusive material, such as, for example, small beads, to facilitate the blockage of the opening 39. The small beads may be strung onto a thread or may be interconnected to each other. In an exemplary embodiment, the material may be prepared in such a way that the expansion occurs only when the material is contacted with a specific type of bonding agent or catalyst.

In an exemplary embodiment, such as the embodiment shown in FIG. 2, the hydrophilic material 38 may be placed on the outer surface of the tubular member 20 or on the inner surface of the balloon 30, preferably at a location proximate the opening 39. The hydrophilic material 38 may be separated from the opening 39 by a suitable distance. The distance may be configured in such a way that, prior to the expansion, the hydrophilic material 38 may not interfere with the passage of air through the opening 39, but, upon contact with the inflation liquid, may sufficiently expand and occlude the opening 39.

FIGS. 4A and 4B show another exemplary embodiment of the invention. In this embodiment, the inside surface of the tubular member 37 may be coated or treated with the hydrophilic material 38', as shown in FIG. 4A. This embodiment may be used in combination with the hydrophilic material 38 placed in the vicinity of the opening 39, as shown in FIG. 2.

The principles of operation relating to the embodiment of FIGS. 4A and 4B may be substantially the same as those described above with reference to FIG. 2. For example, the air may be forced to the distal portion of the balloon 30 and vented out through the opening 39 when the inflation liquid is injection into the catheter 1. Until the inflation liquid reaches the opening 39, the hydrophilic material 38' may remain in its original shape and size without interfering with the air flow though the tubular member 37. Once the inflation liquid reaches the tubular member 37 and makes contact with the hydrophilic material 38' inside the tube 37, the material 38' then rapidly and/or substantially immediately absorbs the inflation liquid and expands to sealingly close the opening 39, as shown in FIG. 4B.

Figure 5:
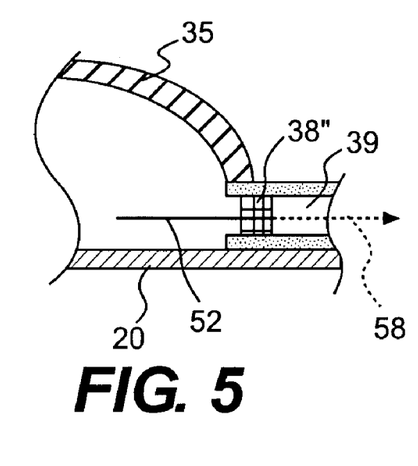
FIG. 5 is a partial exploded cross-sectional view of the distal end portion of an inflatable balloon, according to still another embodiment of the invention.

FIG. 5 shows still another exemplary embodiment of the invention. In this exemplary embodiment, the opening 39 may be provided with a one-way valve 38'', which may selectively allow only the air to pass through the valve 38''. For example, the valve 38'' may include a suitable barrier material that may allow the air to pass through (indicated by dotted arrow 58), while preventing passage of water or vapor (indicated by solid arrow 52). The barrier materials may include, for example, TYVEK® papers (manufactured by Dupont), Porex or porous-type ceramics, GORE-TEX® fabrics, foam or filter material having controlled pore size, or any suitable materials known in the art. The barrier material may also include a hydrophilic material that, upon contact with liquid, may expand and seal the opening 39. In various exemplary embodiments, the hydrophilic material may be coated on or embedded with the barrier material.

A method of operating the catheter 1, according to an embodiment of the invention, will be described in detail with reference to FIGS. 6 through 10. While operational aspects of the invention will be described with an exemplary embodiment of the inflatable balloon shown in FIGS. 2 and 3, and in connection with a particular balloon dilation catheter, the invention may be applied to other suitable medical procedures, or used in connection with any other suitable medical devices, without departing from the scope of the invention. For example, the invention may be used to control bulking of a detachable balloon for use in an embolic device (e.g., when the embolic device is no longer needed) or as a sealing valve. Furthermore, the invention may be applied to other various medical devices, such as, for example, numerous other catheters utilizing the balloon expansion mechanism, such as, for example, stent placement/deployment catheters, dilatationureteral balloon catheters, nephrostomy balloon catheters, or latex balloon occlusion catheters, or other suitable medical devices that require a sealing process, such as, for example, a drug dispensing device for sealing a drug delivery path after dispensing a drug, or that require removal of air or gas from the devices, such as, for example, fluid injection catheters or drug dispensing device.

Figure 6:
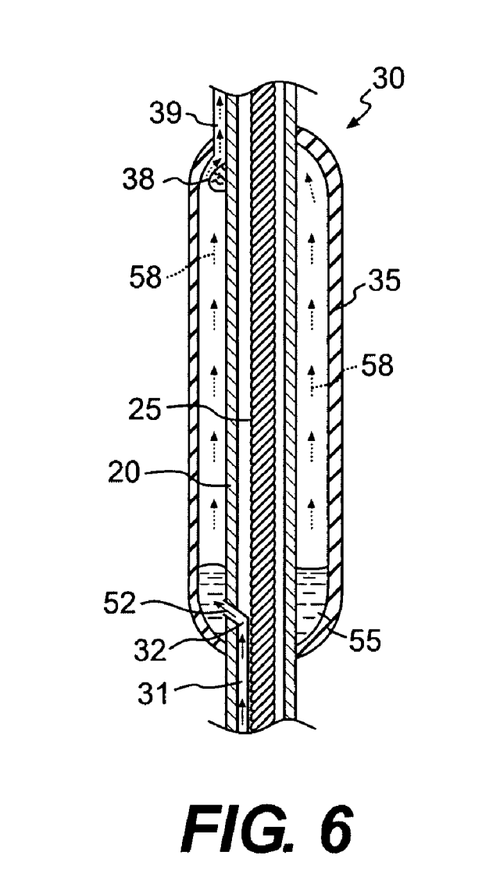
FIGS. 6-10 are schematic cross-sectional views of the inflatable balloon shown in FIG. 2, illustrating an exemplary method of prepping a balloon dilation catheter, according to an embodiment of the invention.
Figure 7:
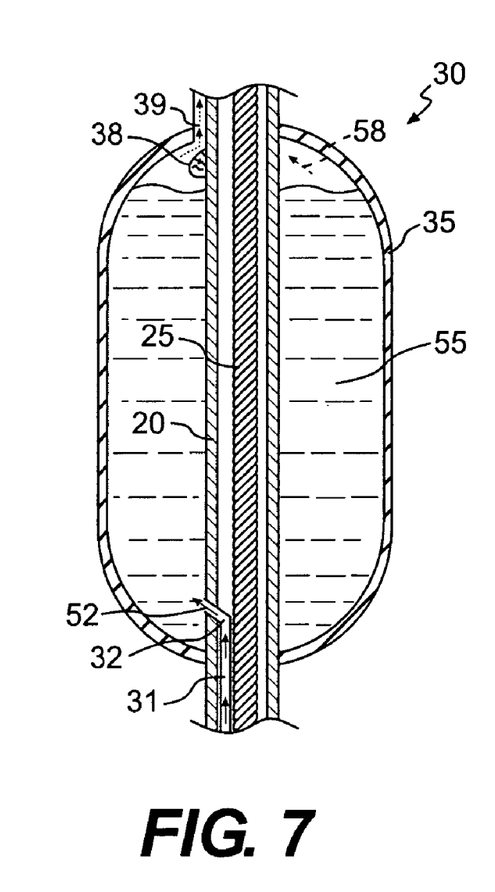
Figure 8:
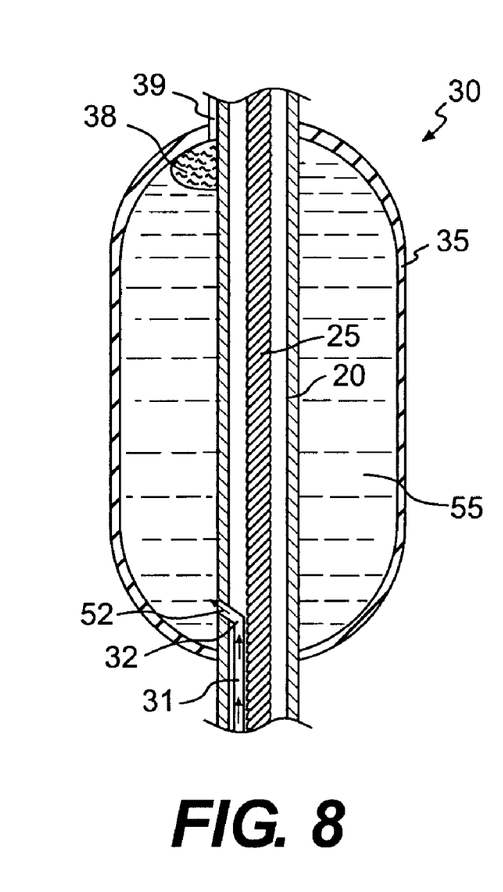

FIGS. 6-10 show schematic cross-sectional views of the inflatable balloon 30 in a vertically oriented position, illustrating various stages of an exemplary prepping procedure performed prior to insertion of catheter 1 into a patient's body. As shown in FIG. 6, injection of the inflation liquid 55 through the fluid lumen 31 and into the balloon 30 may force the air in the lumen 31 and the balloon 30 to the distal portion of the balloon 30. The flow paths of the air and the inflation liquid 55 are indicated with dotted arrows 58 and solid arrows 52, respectively. Injection of the inflation liquid 55 into the balloon 30 may force the air to be vented out of the balloon 30 via the opening 39 formed at the distal-most end of the balloon 30. At this condition, as shown in FIG. 7, the injection of the inflation liquid 55 may cause the balloon 30 to inflate. The degree of inflation and the balloon pressure may be controlled by controlling the flow rate and the amount of the inflation liquid 55 injected into the balloon 30. As more inflation liquid 55 passes into the balloon 30 and more air is vented out of the balloon 30, the liquid level in the balloon 30 may rise to a level where the liquid 55 contacts the hydrophilic material 38. The hydrophilic material 38, upon contact with the inflation liquid 55, may absorb a portion of the inflation liquid 55 and may expand to substantially seal the opening 39, as shown in FIG. 8. At this point, the air that previously existed in the balloon 30 and the lumen 31 has already been removed from the catheter 1.

Figure 9:
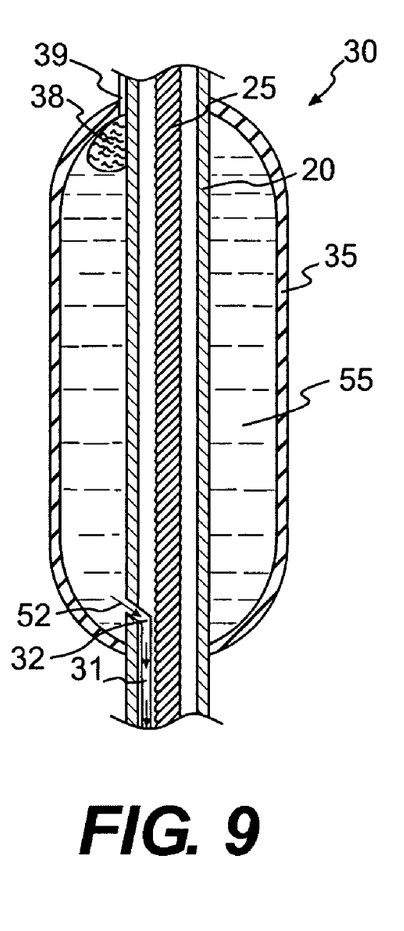

As shown in FIG. 9, after the air is removed from the balloon 30 and the opening 39 is substantially sealed, the balloon 30 may be deflated by withdrawing the inflation liquid 55 back through the fluid port 32. A suitable deflation device, a syringe device or a suction device, connected to the side port 13 of the handle assembly 10 may be used to deflate the balloon 30. In an exemplary embodiment, the same device used to inflate the balloon 30 may be used.

Figure 10:
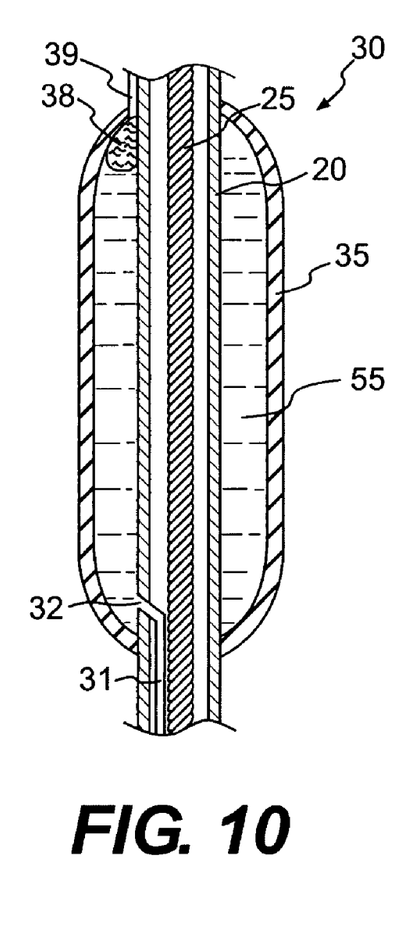

The balloon 30 and the fluid lumen 31 may then be drawn into a vacuum with no air present or they may include only a residual amount of inflation liquid 55 used to prep the catheter, as shown in FIG. 10. With this condition of the balloon 30, the balloon dilation catheter 1 may be inserted into a patient's body for performing the intended procedure.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A balloon assembly for a medical device, comprising:
   an inflatable balloon;
   a fluid port in fluid communication with the inflatable balloon to supply inflation liquid to the inflatable balloon;
   a first opening for selective insertion and removal of a guide wire within the inflatable balloon, the guidewire capable of moving axially relative to the inflatable balloon;
   a second opening for permitting gas to exit the inflatable balloon; and
   an expandable material having a first configuration configured to permit gas to exit through the second opening and a second configuration configured to retain inflation liquid in the inflatable balloon.

2. The assembly of claim 1, wherein the second opening is located at a distal-most end of the inflatable balloon.

3. The assembly of claim 1, wherein the second opening is formed by a hollow tube extending from the inflatable balloon.

4. The assembly of claim 1, wherein the expandable material includes a liquid-activatable material configured to close the second opening upon contact with inflation liquid.

5. The assembly of claim 1, wherein the expandable material is configured to close the second opening after substantially all of the gas is removed from the inflatable balloon through the second opening.

6. The assembly of claim 1, wherein the expandable material is located proximate the second opening.

7. The assembly of claim 1, wherein the expandable material has a material characteristic of expanding in volume from the first configuration to the second configuration upon contact with inflation liquid.

8. The assembly of claim 1, wherein the expandable material is configured to expand from the first configuration to the second configuration in response to contact with a bonding agent or catalyst of an inflation liquid.

9. The assembly of claim 1, wherein the expandable material includes an occlusive material.

10. The assembly of claim 1, wherein the expandable material includes a hydrophilic material placed proximate the second opening.

11. The assembly of claim 1, wherein, prior to the contact with inflation liquid, the expandable material remains in the first configuration without interfering with the passage of gas through the second opening.

12. The assembly of claim 1, wherein the expandable material is spaced from the second opening in the first configuration, so that, prior to contact with inflation liquid, the material does not block the second opening, but after contact with inflation liquid, the material expands to the second configuration and substantially closes the second opening.

13. The assembly of claim 1, wherein the expandable material is disposed in the form selected from the group consisting of particles, coating, porous matrix, fiber bundles, tubular bed, and any combination thereof.

14. The assembly of claim 1, wherein the expandable material is selected from a group consisting of: super absorbent polymers; hydrogel polymers; water-swellable polymers; hydrocolloids; hydrocolloids having polymer compositions of substantially water-insoluble, slightly cross-linked, partially neutralized polymers prepared from unsaturated polymerizable acid group-containing monomers and cross-linking agents; polymer materials that have undergone a cross-linking process; polyacrylates; PEG; polysaccharides; starch or cellulose; generally carboxyl containing polymers; hydrolyzates of starch-acrylonitrile graft copolymers; partially neutralized products of starch-acrylic acid or polyvinyl alcohol graft copolymers; saponification products of vinyl acetate acrylic ester copolymers; derivatives of copolymers of isobutylene and maleic anhydride; hydrolyzates of acrylonitrile copolymers; cross-linked products of hydrolyzates of acrylonitrile copolymers; cross-linked carboxymethyl cellulose; polyaspartate hydrolyzates of acrylamide copolymers; cross-linked products of hydrolyzates of acrylamide copolymers; partially neutralized products of polyacrylic acids; cross-linked products of partially neutralized polyacrylic acids; natural non-ionic polymers; carraggeenan; xanthan gum; gelatin; agar; alginate; and any combination thereof.

15. The assembly of claim 1, wherein the medical device is a balloon dilation catheter.

16. The assembly of claim 1, further comprising the guidewire within the balloon and axially moveable relative to the balloon.

17. A balloon assembly for a medical device, comprising:
an inflatable balloon;
a fluid port in fluid communication with the inflatable balloon to supply inflation liquid to the inflatable balloon;
an opening for permitting gas to exit the inflatable balloon; and
an expandable material having a first configuration configured to permit gas to exit through the opening and a second configuration configured to retain inflation liquid in the inflatable balloon;
wherein the expandable material includes an occlusive material; and
wherein the occlusive material includes a plurality of beads.

18. The assembly of claim 17, wherein the plurality of beads are interconnected.

19. The assembly of claim 17, wherein the plurality of beads in the second configuration block the opening.

20. A dilation catheter comprising:
an elongated tubular member having a distal end and a proximal end;
a proximal handle proximate the proximal end of the tubular member; and
the balloon assembly of claim 1 located proximate the distal end of the tubular member.

21. The catheter of claim 20, wherein the proximal handle includes a connection to a source of inflation liquid.

22. The catheter of claim 21, wherein the tubular member includes a lumen in fluid communication between the source of inflation liquid and the fluid port.

23. The catheter of claim 20, wherein the tubular member defines the fluid port.

24. The catheter of claim 20, wherein the second opening is located at a distal-most end of the inflatable balloon.

25. The catheter of claim 20, wherein the second opening is formed by a hollow tube extending from the inflatable balloon.

26. The catheter of claim 20, wherein the expandable material includes a liquid-activatable material configured to close the second opening upon contact with inflation liquid.

27. The catheter of claim 20, wherein the expandable material is configured to close the second opening after substantially all of the gas is removed from the inflatable balloon through the second opening.

28. The catheter of claim 20, wherein the expandable material is located proximate the second opening.

29. The catheter of claim 20, wherein the expandable material has a material characteristic of expanding in volume from the first configuration to the second configuration upon contact with inflation liquid.

30. The catheter of claim 20, wherein the expandable material is configured to expand from the first configuration to the second configuration in response to contact with a bonding agent or catalyst of an inflation liquid.

31. The catheter of claim 20, wherein the expandable material includes an occlusive material.

32. The catheter of claim 20, wherein the expandable material includes a hydrophilic material placed proximate the second opening.

33. The catheter of claim 20, wherein, prior to the contact with inflation liquid, the self-expandable material remains in the first configuration without interfering with the passage of gas through the second opening.

34. The catheter of claim 20, wherein the expandable material is spaced from the second opening in the first configuration, so that, prior to contact with inflation liquid, the material does not block the second opening, but after contact with inflation liquid, the material expands to the second configuration and substantially closes the second opening.

35. The catheter of claim 20, wherein the expandable material is disposed in the form selected from the group consisting of particles, coating, porous matrix, fiber bundles, tubular bed, or any combination thereof.

36. The catheter of claim 20, wherein the self-expandable material is selected from a group consisting of: super absorbent polymers; hydrogel polymers; water-swellable polymers; hydrocolloids; hydrocolloids having polymer compositions of substantially water-insoluble, slightly cross-linked, partially neutralized polymers prepared from unsaturated polymerizable acid group-containing monomers and cross-linking agents; polymer materials that have undergone a cross-linking process; polyacrylates; PEG; polysaccharides; starch or cellulose; generally carboxyl containing polymers; hydrolyzates of starch-acrylonitrile graft copolymers; partially neutralized products of starch-acrylic acid or polyvinyl alcohol graft copolymers; saponification products of vinyl acetate acrylic ester copolymers; derivatives of copolymers of isobutylene and maleic anhydride; hydrolyzates of acrylonitrile copolymers; cross-linked products of hydrolyzates of acrylonitrile copolymers; cross-linked carboxymethyl cellulose; polyaspartate hydrolyzates of acrylamide copolymers; cross-linked products of hydrolyzates of acrylamide copolymers; partially neutralized products of polyacrylic acids; cross-linked products of partially neutralized polyacrylic acids; natural non-ionic polymers; carraggeenan; xanthan gum; gelatin; agar; alginate; and any combination thereof.

37. A dilation catheter comprising:
an elongated tubular member having a distal end and a proximal end;
a proximal handle proximate the proximal end of the tubular member; and
a balloon assembly located proximate the distal end of the tubular member, comprising:
an inflatable balloon;
a fluid port in fluid communication with the inflatable balloon to supply inflation liquid to the inflatable balloon;
an opening for permitting gas to exit the inflatable balloon; and
an expandable material having a first configuration configured to permit gas to exit through the opening and a second configuration configured to retain inflation liquid in the inflatable balloon;
wherein the expandable material includes an occlusive material; and
wherein the occlusive material includes a plurality of beads.

38. The catheter of claim 37, wherein the plurality of beads are interconnected.

39. The catheter of claim 37, wherein the plurality of beads in the second configuration block the opening.

* * * * *